United States Patent
Roesch et al.

(10) Patent No.: US 8,794,046 B2
(45) Date of Patent: Aug. 5, 2014

(54) METHOD AND DEVICE FOR THE SELF-DIAGNOSIS OF A PARTICLE SENSOR

(75) Inventors: Sabine Roesch, Ditzingen (DE);
Benjamin Gaertner, Neureut (DE);
Johannes Grabis, Renningen (DE);
Alexander Hetznecker, Karlsruhe (DE);
Thorsten Ochs, Schwieberdingen (DE);
Henrik Schittenhelm, Stuttgart (DE)

(73) Assignee: Robert Bosch GmbH, Stuttgart (DE)

(*) Notice: Subject to any disclaimer, the term of this patent is extended or adjusted under 35 U.S.C. 154(b) by 697 days.

(21) Appl. No.: 12/851,124

(22) Filed: Aug. 5, 2010

(65) Prior Publication Data
US 2011/0030451 A1   Feb. 10, 2011

(30) Foreign Application Priority Data
Aug. 5, 2009   (DE) .................. 10 2009 028 239

(51) Int. Cl.
*G01D 18/00*   (2006.01)

(52) U.S. Cl.
USPC ........................................................ 73/1.01

(58) Field of Classification Search
None
See application file for complete search history.

(56) References Cited

U.S. PATENT DOCUMENTS

| | | | |
|---|---|---|---|
| 7,543,477 B2 | 6/2009 | Berger et al. | |
| 2007/0095673 A1* | 5/2007 | Stancovski et al. | 205/341 |
| 2009/0051376 A1 | 2/2009 | Schnell et al. | |

FOREIGN PATENT DOCUMENTS

| | | |
|---|---|---|
| DE | 101 49 333 | 10/2001 |
| DE | 101 33 384 | 1/2003 |
| DE | 103 19 664 | 11/2004 |
| DE | 10 2004 028 997 | 1/2006 |
| EP | 1 925 926 | 5/2008 |

* cited by examiner

*Primary Examiner* — Peter Macchiarolo
*Assistant Examiner* — Alex Devito
(74) *Attorney, Agent, or Firm* — Kenyon & Kenyon LLP

(57) ABSTRACT

Self-diagnosis of a particle sensor may be used for determining a particle content in a gaseous stream. The particle sensor may include at least two interlocking, interdigital electrodes and a heating element. The heating element may be separated from the electrodes by an insulation layer. The particle sensor may be heated in a regeneration phase and a soot load on the particle sensor can thereby be removed. A semiconductive layer may be formed in the insulation layer directly beneath the electrodes by means of external doping or auto-doping. To perform a self-diagnosis, a measurement voltage may be applied at least periodically between the electrodes and a self-diagnostic current may be measured.

12 Claims, 2 Drawing Sheets

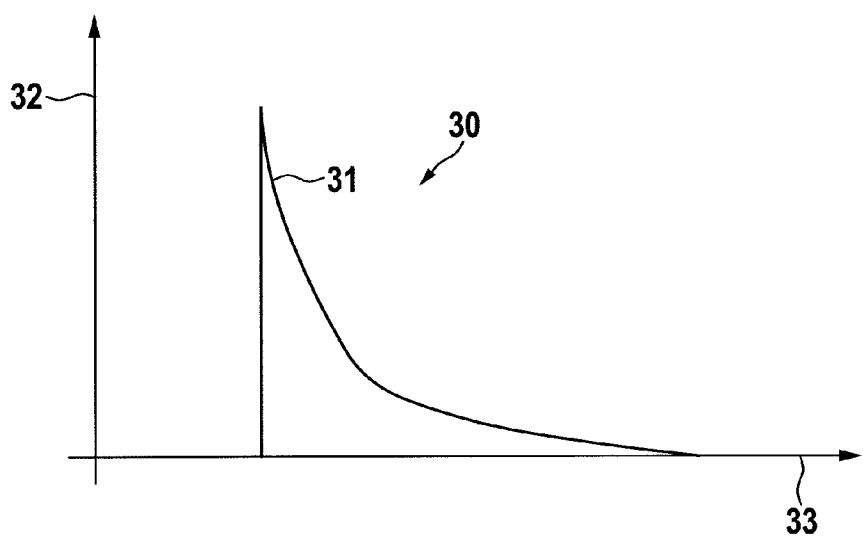

METHOD AND DEVICE FOR THE SELF-DIAGNOSIS OF A PARTICLE SENSOR

This application claims benefit of Serial No. 10 2009 028 239.4, filed 5 Aug. 2009 in Germany and which application is incorporated herein by reference. To the extent appropriate, a claim of priority is made to the above disclosed application.

BACKGROUND

The invention relates to a method for the self-diagnosis of a particle sensor used for determining a particle content in a gaseous stream, wherein the particle sensor includes on its surface at least two interlocking, interdigital electrodes and a heating element separated from said electrodes by an insulation layer. Said particle sensor can be heated by said heating element in a regeneration phase, and a soot concentration can thereby be removed from the same.

The invention furthermore relates to a device for the self-diagnosis of a corresponding particle sensor, said particle sensor being connected to an engine management system or a sensor control unit. Said engine management system or said sensor control unit includes apparatuses for diagnosing the soot concentration on the particle sensor and the particle sensor itself.

Particle sensors are used today, for example, for monitoring the soot discharge of internal combustion engines and for on-board diagnostics (OBD), for example, for monitoring the operation of particle filters. Collecting and resistive particle sensors are thereby known, which evaluate a change in the electrical characteristics of an interdigital electrode structure due to particle depositions. Provision can be made for two or several electrodes, which preferably interlock in a comb-like manner. The electrodes are short-circuited by an increasing number of particles accumulating on the particle sensor, which results in the electrical resistance decreasing as the particle deposition increases, the impedance decreasing or in a change in a parameter, like a voltage and/or a current, which is related to said resistance or said impedance. A threshold value, for example, of a measurement current between the electrodes is generally defined for the evaluation; and the time up until achieving the threshold value is used as a measurement for the deposited particle quantity. As an alternative, a signal rate of change can also be evaluated during the particle deposition. If the particle sensor is fully loaded with soot, the deposited particles are burned off in a regeneration phase with the aid of a heating element integral with said particle sensor.

A resistive particle sensor of this type is described in the German patent publication DE 101 33 384 A1. The particle sensor is constructed from two interlocking, comb-like electrodes, which are at least partially covered by a retaining shell. If particles from a gaseous stream are deposited on the particle sensor, this then leads to an evaluable change in the impedance of the particle sensor, from which the quantity of deposited particles and consequently the quantity of particles carried along in the exhaust gas can be suggested.

The German patent publication DE 101 49 333 A1 describes a sensor device for measuring the humidity of gases, comprising a resistance measurement structure disposed on a substrate. Said measurement structure interacts thereby with a soot layer and a temperature measuring device is provided. The soot concentration in the exhaust gas of an internal combustion engine can likewise be determined with said sensor device.

A method for controlling the particle deposition on a sensor element, which includes a first electrode and an additional electrode and at which a first voltage $U_1$ as well as a second voltage $U_2$ can be applied at voltage terminals, is known from the German patent publication DE 10 2004 028 997. Provision is thereby made for the sensor element to be able to be operated with an increased voltage $U_1$ during a first time period $t_1$ and after exceeding a triggering threshold AP of the sensor element for said sensor element to be able to be operated at a lower voltage $U_2$, which is lower than the increased voltage $U_1$. The method makes it possible for the time after a regeneration of the sensor element, in which no measurement signal is available, up until the point in time, whereat an evaluable signal is received as a result of a deposition of a sufficient quantity of particles, to be shortened by operating the sensor element with an increased operating voltage during this phase. The increased operating voltage leads to an increased rate of deposition of the particles on the sensor element. If a sufficiently large quantity of particles has been deposited on the sensor element, thereby enabling a usable measurement signal to be present, the sensor element is operated with a lower voltage having a correspondingly lower particle deposition rate so that the measuring time until the next necessary regeneration of the sensor element is lengthened. The method thus provides for two consecutive operating phases, a first phase with increased operating voltage, during which a sufficient measurement signal is still not present, and a second phase with reduced voltage, during which the actual measurement of the particle concentration takes place. In the process, the resistance or the impedance of the sensor element is determined during both phases via an appropriate current measurement, in the one instance to recognize the triggering threshold and in the other to determine the particle deposition rate. A defined particle deposition is necessary in both phases. The selected voltages thus represent in both phases a compromise between optimized particle deposition and a precise resistance or impedance measurement.

A sensor is known from the German patent publication DE 103 19 664 A1 for the detection of particles in a gaseous stream, particularly of soot particles in an exhaust gas stream, which is disposed on a substrate made of an electrically insulating material. Provision is thereby made for the measuring electrodes to be coated with a protective layer. The electrodes are protected from corrosion at harsh ambient temperatures by said protective layer. Said protective layer can thereby be implemented in an electrically conductive manner or as an electrical insulator. A conductive protective layer allows for the particle concentration to be determined by means of a resistive direct current measurement, a parallel connection between the electrodes resulting via the protective layer and the deposited particles. When an insulating protective layer is implemented, an impedance measurement with the aid of AC voltage is required.

In order to regenerate the particle sensor after particle deposition has taken place, the particle deposits have to be burned off said sensor with the aid of an integrated heating element. This process has to be implemented at specific time intervals in order to avoid discrepancies when determining the particle concentration.

In an additional application with the internal file number R.318399, the applicant, for example, provides for the self-diagnosis by having the particle sensor include an additional flat test electrode. Provision is then made in multiple procedural steps for different test voltages to be applied between the measuring electrodes and the test electrode and in each case for the current, respectively capacitance, to be measured and using the ascertained values for an inference to be made as to whether the particle sensor is functioning properly.

The European patent publication EP 1 925 926 A1 describes a device and an evaluation process for checking the functional capability, respectively for checking the plausibility, of a sensor based on an electrode system, in particular a particle sensor, the device comprising at least one reference electrode system. The evaluation process thereby provides for comparative measurements at the measuring electrodes as well as at the reference electrodes, a proper functioning of the sensor being suggested on the basis of the ascertained values.

Because the particle sensor is disposed downstream of a particle filter in the exhaust gas stream when used for on-board diagnostics, particles, in particular soot particles, which could yield a corresponding sensor signal, should no longer be found in the exhaust gas at that location, whereat the particle filter is disposed, when said particle filter is fully operational. The fact that the sensor does not deliver a signal can, however, also mean that the particle sensor is defective, and a particle filter, which is likewise possibly defective, is not recognized as being defective.

It is therefore the aim of the invention to provide a method, which allows for a reliable self-diagnosis of the particle filter, particularly when installed in the aforementioned position.

It is furthermore the aim of the invention to provide an appropriate device for carrying out the method.

SUMMARY

The aim relating to the method is met by the characteristics of the claims 1 to 5.

The aim relating to the device is thereby met in that the engine management system or the sensor control unit includes apparatuses for evaluating a self-diagnostic current when an AC or DC voltage is applied as the measurement voltage to the electrodes; and in that when DC voltage is used as the measurement voltage, the particle sensor can be heated for a short time to temperatures >500° C. by means of the engine management system or the sensor control unit for the purpose of performing a self-diagnosis of said sensor.

Provision is thereby made in the method according to the invention for a semiconductive layer to be formed by means of external doping or auto-doping in the insulation layer directly beneath the electrodes and as part of the self-diagnosis for a measurement voltage to be applied at least periodically between the electrodes and a self-diagnostic current to be measured.

This approach is advantageous because a diagnosis of the functional capability of the measuring electrodes of the particle sensor can be carried out. By means of a self-diagnosis of this type, it is possible to recognize defective particle sensors, whose electrodes were damaged during manufacture or when used beyond the service life of the sensor, and to compensate for the error by a corresponding correction of the measured particle signal or to inform the driver/operator of the vehicle/equipment thereof in the case of a total breakdown by way of optical or acoustical warnings. This is particularly advantageous for particle sensors, which are installed downstream of a particle filter when viewed from the direction of flow of the exhaust gas, and it is thereby unclear whether the particle sensor is functioning properly and whether the exhaust gas has only a slight or no proportion of soot or whether the particle sensor is faulty and the exhaust gas is in fact possibly heavily loaded with soot. The operational testing of the sensor takes place in an advantageous manner during the final check before delivery to the customer as well as during an operation "free of soot", i.e. in an operational phase of the vehicle/equipment, wherein no soot particles are released, which could possibly falsify the measurement values.

The particle sensor includes at least in some regions a semiconductive layer in an insulating support layer directly beneath the electrodes. Said semiconductive layer is produced by auto-doping and/or by an external doping of the insulating support layer with sodium ions and/or with other readily mobile ions, e.g. lithium ions, which proportionally range from 100 ppm to 10000 ppm in the insulating support layer. By means of this doping, a certain amount of conductivity can be produced, particularly at high temperatures, in the semiconductive layer by the mobility of the ions being increased by means of this temperature application. The properties of the semiconductive layer with respect to the temperature dependent resistance can be predetermined through the concentration and selection of the ions.

Layers produced in this manner therefore have electrical resistances in the range of >100 M$\Omega$ between the electrodes during the measuring operation (soot collecting) at approximately 400° C. If this layer is heated up for diagnostic purposes, for example to approximately 850° C., the resistance drops to 0.2 to 1 M$\Omega$, which corresponds to a current of approximately 10 to 50 µA at a measurement voltage of 10 V DC. This current can be used as a measurement for the quality and performance of the particle sensor.

In a modification to the embodiment, the external doping of the insulating support layer to produce the semiconductive layer under the electrodes is achieved by sodium impurities from the electrodes, which were attached in the manufacturing process. In so doing, this rather undesired effect is specifically used for doping. An additional doping process can thereby be eliminated.

Provision is made in another modification to the embodiment for the auto-doping of the insulating support layer to produce the semiconductive layer under the electrodes to be achieved by the specific introduction of sodium ions and/or other readily mobile ions into the insulating support layer. This is, of course, more complicated when compared to the first modification, is, however, advantageous with regard to a defined doping.

In order to insulate the semiconductive layer of the particle sensor in a downward direction within the layer structure, an insulation layer of pure aluminum oxide can be inserted beneath the semiconductive layer. An effective separation from functional layers, which lie deeper in the sensor structure and, as the case may be, likewise have semiconductive properties, can thereby be achieved.

In addition, an additional layer of aluminum oxide doped with barium can be inserted under the insulation layer of pure aluminum oxide. A particularly effective barrier layer, especially for the readily mobile sodium ions, is formed with said additional layer.

If an AC voltage is applied between the electrodes as a measurement voltage for the self-diagnosis, a simple evaluation of the self-diagnostic current results, with which the circuit complexity of the evaluation is considerably reduced.

Provision is made in another modification to the method for a DC voltage to be applied between the electrodes as a measurement voltage for the self-diagnosis and for the particle sensor to be heated with the heating element to temperatures >500° C., preferably to approximately 850° C. prior to and after applying said DC voltage. In a preferred modification to the method, the heating of the particle sensor to the aforementioned temperatures takes place for at least 30 seconds, typically for approximately one minute.

By applying a DC voltage, which can be advantageous particularly in motor vehicles, a polarization effect normally occurs, which results in the continual decrease of the conductivity of the semiconductive layer. Said conductivity can again be regenerated by the heating of the sensor. This measure has thus the effect that the readily mobile ions can again be evenly distributed within the semiconductive layer and consequently the polarization can again be removed. A transfer pulse of 1 to 1000 ms duration at approximately −10 V DC can additionally be impressed in order to achieve an active regeneration. The maximum value of the measured self-diagnostic current, which results immediately upon applying the measurement voltage, can be used as a measurement for the quality and performance of the particle sensor with its electrodes in this modification to the method.

Provision is made in a further preferred modification to the method for the supply of DC voltage to the electrodes to be implemented only for a short time span in the range of 1 ms to 100 ms. This has the advantage that the semiconductive layer is only slightly polarized in these short time intervals, and therefore a plurality of measurement cycles (for example up to 1000 cycles) are possible over longer periods of time until a regeneration again has to take place.

A preferred application of the modification to the method, as it was previously described, provides for the regeneration of the particle sensor within the scope of an on-board diagnosis of a diesel internal combustion engine. This application deals particularly with a precise and reproducible diagnosis of the particle loading of a soot particle filter (DPF) disposed in the exhaust gas tract of the diesel internal combustion engine.

BRIEF DESCRIPTION OF THE DRAWINGS

The invention is explained below in detail using an exemplary embodiment depicted in the figures. The following are shown:

FIG. 2 is an exploded view of a particle sensor in a schematic depiction and FIG. 3 is a measurement diagram for the self-diagnosis of the particle sensor.

DETAILED DESCRIPTION

Figure 1:
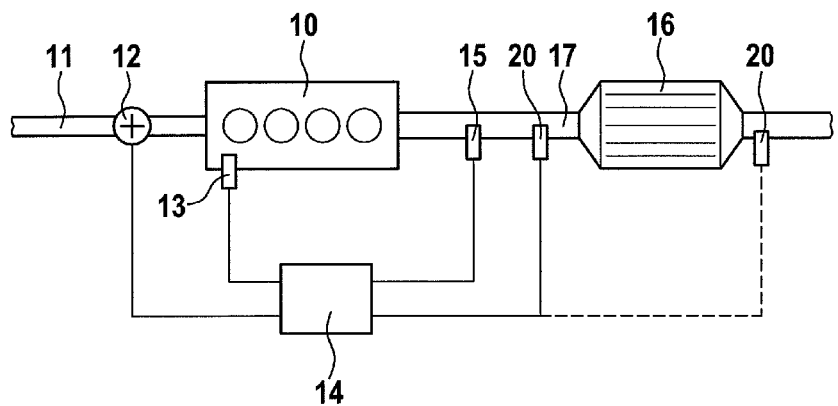
FIG. 1 is the technical environment, in which the method can be used, in a schematic depiction.

FIG. 1 schematically shows the technical environment, in which the method according to the invention can be used. An internal combustion engine 10, which can be embodied as a diesel engine, is supplied with combustion air via an air supply 11. The air volume of the combustion air can thereby be determined by means of an air mass flow meter 12 in the air supply 11. The air volume can be used for correcting a deposition probability of the particles present in the exhaust gas of the internal combustion engine 10. The exhaust gas of the internal combustion engine 10 is discharged via an exhaust gas tract 17, wherein an emission control system 16 is disposed. Said emission control system 16 can be embodied as a diesel particle filter. An exhaust gas probe 15 embodied as a lambda probe and a particle sensor 20, whose signals are supplied to an engine management system 14, are furthermore disposed in said exhaust gas tract 17. The engine management system 14 is furthermore connected to the air mass flow meter 12 and specifies on the basis of the data, with which it is provided, a fuel quantity, which can be supplied via a fuel metering 13 of the internal combustion engine 10.

The particle sensor 20 can also thereby be disposed behind the exhaust gas emission control system 16 in the direction of flow of the exhaust gas. This disposal has advantages with regard to a homogenization of the exhaust gas flow at this location, and this is particularly the case when used within the scope of an on-board diagnosis. An observation of the particle discharge of the internal combustion engine 10 and a projection of the loading of the emission control system 16, which is configured as a diesel particle filter (DPF), are possible with the devices shown.

Figure 2:
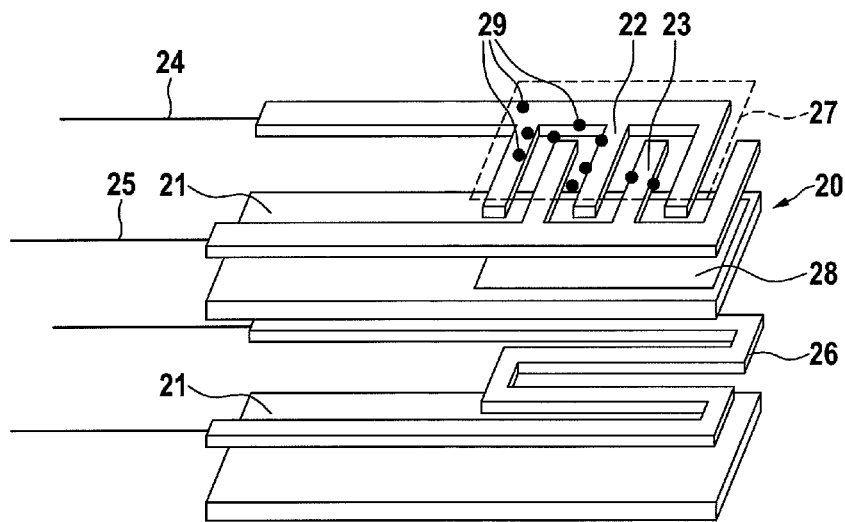

In a schematic depiction, FIG. 2 shows an exploded view of a particle sensor 20 according to the technical field.

A first electrode 22 and a second electrode 23 are attached to insulating support layers 21, for example, of aluminum oxide. The electrodes 22, 23 are embodied in the form of two interdigital, interlocking comb electrodes. A first terminal 24 and a second terminal 25, via which said electrodes 22, 23 can be connected to an undepicted sensor control unit for the voltage supply and for carrying out the measurement, are provided at the front ends of said electrodes 22, 23.

In addition, a heating element 26, which is connected to the sensor control unit via additional terminals, is integrated between the insulating support layers 21 in the example shown.

If a particle sensor 20 of this type is operated in a gaseous stream carrying particles 29, for example, in an exhaust gas passage of a diesel engine or a furnace, particles 29 from the gaseous stream are then deposited on the particle sensor 20. In the case of the diesel engine, the particles 29 relate to soot particles with a corresponding electrical conductivity. Besides being dependent on the particle concentration in the exhaust gas, the deposition rate of the particles 29 on the particle sensor 20 also thereby depends among other things on the voltage, which is present at the electrodes 22, 23. An electrical field is generated by said voltage present at the electrodes 22, 23, which exerts a corresponding attractive force on electrically charged particles 29 and on particles 29 with a dipole charge. The deposition rate of the particles 29 can for that reason be manipulated by means of the suitable selection of the voltage present at the electrodes 22, 23.

In the exemplary embodiment, the electrodes 22, 23 and the uppermost insulating support layer 21, whereupon said electrodes 22, 23 are situated, are coated with a protective layer 27. This optional protective layer 27 protects said electrodes 22, 23 from corrosion at the predominately prevailing high operating temperatures of the particle sensor 20. It is manufactured from a material with low conductivity in the present exemplary embodiment. Said protective layer 27 can, however, also be manufactured from an insulator.

Particles 29 from the gaseous stream have been deposited on the protective layer 27 in the form of a layer. As a result of the slightly conductive protective layer 27, said particles 29 form a conductive pathway between the electrodes 22, 23 so that a change in resistance between the electrodes 22, 23 occurs as a function of the quantity of deposited particles 29. Said change in resistance can, for example, be measured by a constant voltage being applied to the terminals 24, 25 of the electrodes 22, 23 and the change in the current resulting from the deposited particles 29 being determined.

If the protective layer 27 is constructed in an electrically insulated manner, the deposited particles 29 lead to a change in the impedance of the particle sensor 20, which can be evaluated by a corresponding measurement, preferably with an AC voltage.

If the particle sensor 20 is covered with a layer of particles 29 to such an extent that additionally deposited particles 29 do not lead to any additional change in the resistance, respectively impedance, of the particle sensor 20, the particle sensor 20 is then regenerated within a regeneration phase. For this purpose the particle sensor 20 is heated with the aid of the heating element 26 to such an extent that the attached particles are burned off. In a first phase after the regeneration, if only a small amount of particles 29 are present on the particle sensor 20, a meaningful resistance or impedance measurement is not possible. Only after a sufficient length of time are enough particles 29 attached to the particle sensor 20 that a closed current path is formed between the electrodes 22, 23 via the particles 29 and a measurement is possible. Known evaluation methods specify the time from a regeneration of the particle sensor 20 up until a predetermined threshold of the measurement signal is achieved, for example, a predetermined current value, in order to ascertain a conclusion about the particle concentration in the gaseous stream. Alternative methods use the signal rate of change after achieving a minimum signal for determining the particle concentration.

The uppermost insulating support layer 21, whereupon the electrodes 22, 23 are situated, is additionally doped according to the method, thus enabling a semiconductive layer 28 to form. Said layer 28 can, for example, be formed as follows:

Option 1:

The insulating support layer 21, which is formed from pure aluminum oxide, is situated beneath the electrodes 22, 23. Said insulating support layer 21 is contaminated with sodium impurities if the electrodes 22, 23, which are typically configured as platinum measuring electrodes, are attached. The semiconductive layer 28 thus forms in the region of the electrodes 22, 23. Said electrodes 22, 23 can be especially easily and cost effectively applied to the insulating support layer 21 by means of a screen printing process and fixedly attached to the same by a subsequent penetration process. In so doing, the sodium ions can diffuse into said insulating support layer 21 and form the semiconductive layer.

Option 2:

The insulating support layer 21, which is formed from pure aluminum oxide, is situated beneath the electrodes 22, 23. Sodium ions are introduced into said insulating support layer 21 by means of targeted doping. The concentration of the sodium ions in the insulating support layer 21 amounts to between 100 ppm and 10000 ppm in the doping zone, which forms the semiconductive layer 28. This value lies typically at approximately 1000 ppm. Other readily mobile ions as, for example, lithium can also in principle be introduced as a dopant.

Option 3:

As embodied in option 2, the insulating support layer 21 is enriched by targeted doping with sodium ions and therefore forms the semiconductive layer. In order to insulate the semiconductive layer 28 in a downward direction from other functional layers of the particle sensor 20, an additional layer of aluminum oxide is inserted directly beneath the semiconductive layer 28. In addition, still another layer of barium-doped aluminum oxide, which particularly acts as a barrier layer for the readily mobile sodium ions, can be inserted beneath said additional layer.

In the context of a self-diagnosis, the inventive method thereby provides for a measurement voltage to be applied at least periodically between the electrodes 22, 23 and for a self-diagnostic current 31, which flows through the electrodes 22, 23 and the semiconductive layer, to be measured, said self-diagnostic current 31 being a measurement for the functional operability of the particle sensor 20, respectively for its quality.

In this connection, provision is made in a modification to the method for an AC voltage to be applied between the electrodes 22, 23 as the measurement voltage for the self-diagnosis.

Provision is made in another modification to the method for a DC voltage to be applied between the electrodes 22, 23 as the measurement voltage for the self-diagnosis. Due to the effects of polarization, the self-diagnostic current 31 steadily decreases in this modification after applying the measurement voltage. For that reason, provision is made for the particle sensor 20 to be heated via the heating element 26 to temperatures >500° C., typically to approximately 850° C. prior to and after application of the DC voltage so that the semiconductive layer 28 can thereby again regenerate. In so doing, the sodium ions can again be evenly distributed in the semiconductive layer 28, thereby enabling the polarization to again be removed. This heating of the particle sensor 20, which serves the regeneration thereof, is usually implemented for at least 30 seconds, typically for about 1 minute. This regeneration temperature can at the same time be monitored and regulated by means of a meander line resistor (platinum resistor), which is usually integrated in the particle sensor 20 for monitoring temperature. Provision can also be made for the temperature-dependent resistor of the heating element 26 to be used for the monitoring of temperature, respectively temperature regulation.

When a DC voltage is applied to the electrodes 22, 23, a modification to the method provides for said DC voltage to be present at said electrodes 22, 23 for only a short time in the range of 1 ms to 100 ms, typically for 10 ms.

FIG. 3 shows a measurement diagram 30 by way of example, with which the temporal course of the self-diagnostic current 31 is depicted. A current 32 is plotted versus the time 33, said current 32 flowing across the electrodes 22, 23 and through the semiconductive layer 28 if the measurement voltage is applied.

A DC voltage of 10 V is applied as the measurement voltage in the example shown. The self-diagnostic current initially increases to values between 10 μA and 50 μA depending upon the doping of the semiconductive layer 28 and drops within about 10 s steadily to zero due to the effects of polarization. The amount of the initial value for the self-diagnostic current 31 can be used as proof for the functional capability of the particle sensor 20.

The invention claimed is:

1. Method for the self-diagnosis of a particle sensor used for determining a particle content in a gaseous stream, wherein the particle sensor includes at least two interlocking, interdigital electrodes and a heating element, which is separated from said electrodes by an insulation layer and with which the particle sensor is heated in a regeneration phase and a soot load on said particle sensor can thereby be removed, wherein a semiconductive layer is formed in the insulation layer directly beneath the at least two electrodes by means of external doping or auto-doping of the insulation layer and in order to perform said self-diagnosis, a measurement voltage is applied at least periodically between said electrodes and a self-diagnostic current is measured.

2. The method according to claim 1, wherein an AC voltage is applied between the electrodes as a measurement voltage for performing the self-diagnosis.

3. The method according to claim 1, wherein a DC voltage is applied between the electrodes as the measurement voltage for performing the self-diagnosis and the particle sensor is heated via the heating element to temperatures >500° C. prior to and after applying said DC voltage.

4. The method according to claim 3, wherein the heating of the particle sensor to temperatures >500° C. is implemented for at least 30 seconds.

5. The method according to claim 3, wherein the application of a DC voltage to the electrodes is implemented only for a short time span in the range of 1 ms to 100 ms.

6. Application of the method according to claim 1, within the scope of an on-board diagnosis of a diesel internal combustion engine.

7. Device for a self-diagnosis of a particle sensor used for determining a particle content in a gaseous stream, said particle sensor including on its surface at least two interlocking, interdigital electrodes and a heating element, which is separated from said electrodes by an insulation layer and with which the particle sensor is heated in a regeneration phase and a soot concentration on said particle sensor can thereby be removed,
    said particle sensor including a semiconductive layer at least in some regions directly beneath the at least two electrodes in an insulating support layer, said semiconductive layer being produced by auto-doping and/or by an external doping of said insulating support layer,
    said particle sensor being connected to an engine management system or a sensor control unit and said engine management system or said sensor control unit including apparatuses for diagnosing the soot concentration on said particle sensor or said particle sensor itself, wherein said engine management system or said sensor control unit includes apparatuses for evaluating a self-diagnostic current when applying an AC or DC voltage as a measurement voltage to said electrodes and in that when using DC voltage as the measurement voltage, said particle sensor can be heated for a short time to temperatures >500° C. via said engine management system or said sensor control unit in order to perform the self-diagnosis.

8. The device according to claim 7, wherein said semiconductive layer being produced by auto-doping and/or by an external doping of said insulating support layer with sodium ions and/or other readily mobile ions, which proportionally range from 100 ppm to 10000 ppm in said insulating support layer.

9. The device according to claim 8, wherein the external doping of the insulating support layer to produce the semiconductive layer beneath the electrodes is achieved by sodium impurities from the electrodes attached during the manufacturing process.

10. The device according to claim 8, wherein the auto-doping of the insulating support layer to produce the semiconductive layer beneath the electrodes is achieved by the targeted insertion of sodium ions and or other readily mobile ions into the insulating support layer.

11. The device according to claim 8, wherein an insulation layer of pure aluminum oxide is inserted beneath the semiconductive layer.

12. The device according to claim 11, wherein an additional layer of aluminum oxide doped with barium is inserted beneath the insulation layer of pure aluminum oxide.

* * * * *